United States Patent [19]
Roberts

[11] Patent Number: 5,234,919
[45] Date of Patent: Aug. 10, 1993

[54] WATER SOLUBLE, HIGHLY ACTIVE DIMETHOATE FORMULATIONS IN AN ALCOHOL/ESTER SOLVENT SYSTEM

[75] Inventor: Johnnie R. Roberts, Memphis, Tenn.

[73] Assignee: Helena Chemical Company, Memphis, Tenn.

[21] Appl. No.: 739,399

[22] Filed: Aug. 2, 1991

[51] Int. Cl.$^5$ ............................................. A01N 57/00
[52] U.S. Cl. ..................................................... 514/119
[58] Field of Search ......................................... 514/119

[56] References Cited

U.S. PATENT DOCUMENTS

| | | | |
|---|---|---|---|
| 3,317,374 | 5/1967 | Walrand et al. | 514/119 |
| 3,726,975 | 4/1973 | Bassand | 514/119 |

OTHER PUBLICATIONS

Trotter et al., C.A. vol. 103 (1985) 103:155693x.

*Primary Examiner*—Allen J. Robinson
*Attorney, Agent, or Firm*—Connolly and Hutz

[57] ABSTRACT

A water soluble, highly active formulation of O,O-dimethyl S-(N-methylcarbamyl) phosphorodithioate in a solvent system comprising a lower alkyl alchol and a lower alkyl acetate ester is disclosed. The formulations of the present invention are completely water soluble, even in the absence of emulsifiers or other dispersing agents. They contain greater amounts of the active ingredient and display greater tolerance to low temperatures. The mixed solvent system used in these formulations is desirable since it is less toxic than the known solvents.

10 Claims, No Drawings

WATER SOLUBLE, HIGHLY ACTIVE DIMETHOATE FORMULATIONS IN AN ALCOHOL/ESTER SOLVENT SYSTEM

The present invention relates to the field of agricultural, forestry, turf, ornamental, industrial, aquatic, rights-of-ways and other applications where insecticides are used and, more specifically, to water soluble, highly active O,O-dimethyl S-(N-methylcarbamyl) phosphorodithioate formulations.

BACKGROUND OF THE INVENTION

O,O-dimethyl S-(N-methylcarbamyl) phosphorodithioate ("dimethoate") is a known pesticide and is available as an emulsifiable concentrate containing an emulsifier and an organic nonaqueous solvent. Consumers dilute the concentrate to form emulsions since the known concentrates are insoluble in water. The resulting mixture is sprayed during agricultural applications.

A pesticidal composition is disclosed in U.S. Pat. No. 3,090,719 that comprises O,O-dimethyldithiophosphorylacetic acid N-monoethylamide, an emulsifier and a solvent that can be cellosolve acetate or a mixture of several other organic solvents such as xylene, primary amyl acetate, carbitol acetate or glycol ether acetate. The patent discloses that it is desirable to exclude solvents containing hydroxy groups to provide more stable compositions.

In U.S. Pat. No. 3,197,362, formulations of O,O-dimethyldithiophosphorylacetic acid N-monoethylamide with a high content of active component and stable at low temperatures are disclosed. The improved characteristics are achieved by use of solvents belonging to the class of aromatic hydrocarbons, aliphatic and cyclic ketones, primary alcohol acetates and glycoethers and trialkylphosphoric esters. Examples of formulations using lower alkyl alcohol solvents are disclosed for comparison purposes.

Liquid anhydrous pesticidal concentrates containing N-methyl-N-formyl amide of O,O-dimethyldithiophosphoryl acetic acid are disclosed in U.S. Pat. No. 3,716,636 wherein the composition is stabilized with an acid anhydride such as acetic anhydride. The composition can also include solvents such as ketones, ethers, esters, hydrocarbons or mixtures thereof. The use of any alcohol as a solvent is not disclosed.

Mixtures of xylene hydrocarbons and cyclohexanone have been used as a solvent system for dimethoate. However, such formulations are unsatisfactory for several reasons. There are limitations to the amount of dimethoate that can be dissolved in cyclohexanone. The most concentrated formulation commercially available at this time contains 4 pounds of dimethoate per gallon of the formulation. Both xylene hydrocarbons and cyclohexanone are toxic materials presenting environmental hazards in production, use and disposal. Known formulations of dimethoate have relatively high freeze points (35°–45° F.) which limit their use in cold weather.

Formation of the emulsions requires the presence of emulsifying agents to create the dispersion of the insoluble concentrate in water. These dispersions are not stable for long periods of time and stratify with different levels of insecticide in the spray mix, possibly resulting in inconsistent spray application. Poor agitation of the diluted spray mix prior to application can result in separation of the dimethoate from the emulsion.

It is the object of this invention to provide a formulation of dimethoate that is water soluble, highly active and tolerant of low temperatures wherein an emulsifier is not required and the solvent system is less toxic to man and animals than solvents used previously.

SUMMARY OF THE INVENTION

The present invention is a water soluble, highly active formulation of O,O-dimethyl S-(N-methylcarbamyl) phosphorodithioate in a solvent system comprising a lower alkyl alcohol and a lower alkyl acetate ester. The formulations of the present invention are completely water soluble, even in the absence of emulsifiers or other dispersing agents. They contain greater amounts of the active ingredient and display greater tolerance to low temperatures than the known formulations of the prior art. The mixed solvent system used in these formulations is desirable since it is less toxic than the known solvents.

DETAILED DESCRIPTION OF THE INVENTION

The present invention is a water soluble highly active dimethoate formulation that is less toxic than known dimethoate formulations. The formulations of this invention comprise O,O-dimethyl S-(N-methylcarbamyl) phosphorodithioate in a solvent system comprising an aliphatic $C_1$–$C_8$ alcohol and an acetate ester of an aliphatic $C_1$–$C_8$ alcohol.

The active ingredient, O,O-dimethyl S-(N-methylcarbamyl) phosphorodithioate (dimethoate) is well known in the art. Formulations containing dimethoate are diluted in water and subsequently sprayed for agricultural applications. Typical commercially available formulations of dimethoate contain from about 20.0% to about 45% by weight dimethoate. The dimethoate formulations of the present invention contain from about 1 to about 70% by weight of dimethoate based on the weight of the formulation, preferably from about 45.0 to about 60.0% by weight, most preferably from about 56.5 to about 57.5% by weight. The solvent system used in the formulations of the present invention comprise a lower alkyl alcohol and a lower alkyl acetate ester. Suitable lower alkyl groups are those containing from 1 to 8 carbon atoms, preferably 1 to 4 carbon atoms, most preferably 2 to 4 carbon atoms. Useful alcohols include methanol, ethanol, propanol, isopropyl alcohol and all isomers of butanol, pentanol, hexanol, heptanol, and octanol. The preferred alcohols are ethanol, propanol, isopropyl alcohol and butanol. To avoid degradation problems with the alcohol component of the solvent mixture of the present invention, the alcohol used is essentially anhydrous and contains no more than 0.15% water by weight. Suitable acetate esters include methyl acetate, ethyl acetate, propyl acetate and all isomers of butyl acetate. The preferred esters are ethyl acetate, propyl acetate and butyl acetate. The solvent mixture should be essentially anhydrous and relatively pure to assure maximum shelf life of the formulation.

The ratio of ester to alcohol will vary for different ester/alcohol combinations and according to the amount of dimethoate present. The ratio of ester to alcohol is about 5:95 to about 95:5. The optimum ratio is determined by preparing small portions of solutions containing the desired amount of dimethoate and adding various ratios of ester/alcohol mixtures to each and then evaluate the resulting solution for temperature stability and water solubility. For example, the optimum ratio of ester to alcohol for a mixture of ethyl acetate and ethanol for a 58.0% by weight formulation of dimethoate is 1:4. In formulations containing 20.5% by weight of dimethoate, the ratio of ethyl acetate and ethanol would be about 4:1.

Other ingredients can be added to the formulations of the present invention to enhance product performance or stability of the dimethoate. Stabilizers such as those described in U.S. Pat. No. 3,716,636, herein incorporated by reference, can be added to the formulation. Acetic anhydride is an example of a useful stabilizer. The stabilizers are typically added in an amount from about 0.50 to about 3.5% by weight of the formulation. Formulations containing such a stabilizer are useful in applications involving storage in hot humid areas as in parts of the world having tropical climates.

As noted previously, the formulations of the invention do not require the use of emulsifiers or dispersing agents for water solubility or dispersion. Known dimethoate concentrates presently available are insoluble in water and require the use of emulsifying agents to disperse the dimethoate concentrate in water. The dimethoate formulations according to the present invention are 100% water soluble and result in a true solution when the formulation is mixed with water. As a result, prolonged agitation is not required and a more uniform and consistent spray mix is obtained without stratification of the active ingredient from top to bottom. There is improved compatibility of the dimethoate formulation with other possible ingredients in the spray mix such as fertilizers and plant micronutrients. Since a true solution is formed, the spray mix is not sensitive to factors such as water hardness, salt content, pH, and silt content that can be detrimental to the emulsions formed from known dimethoate concentrates.

Formulations according to the present invention are prepared by dissolving dimethoate in the solvent mixture. For ease of mixing, the following order of adding the ingredients is preferred: alcohol, ester then dimethoate. As the concentrations of dimethoate approach the 40 to 60% range, the temperature of the formulation drops about 6° to 10° C. To maintain the solubility of the dimethoate, external heat can be applied to the mixing vessel to maintain the temperature in the range of about 32° to about 38° C. during mixing. The presence of sufficient amounts of ferric and ferrous ions can catalyze decomposition of the dimethoate, therefore, the formulations are preferably prepared in equipment made from stainless steel, polyethylene, polypropylene, or glass. To avoid degradation problems and maximize shelf life, the moisture content of the dimethoate formulation should not exceed about 0.25% by weight of the formulation.

In some applications of the dimethoate insecticide concentrates, the addition of surfactants is desired because of the high tension values and hydrophobic surface of most plant tissues. The compositions of the present invention provide a means of delivering such surfactants as integral components of dimethoate concentrates since the compositions require no emulsifiers and the solvent system is compatible with the surfactants. The surfactants are selected from the following known surfactants:

(1) Ethoxylated Fatty Acids

R = alkyl group with 6 to 12 carbons
n = 1–20 moles of ethylene oxide (2) Alkyl Ethoxylates R—O(CH$_2$CH$_2$O)$_x$H
R = C$_1$ to C$_{15}$ Alkyl group
x = 1 to 20

(3) Alkyl Phenol Ethoxylates

R = H or C$_6$ to C$_{12}$ Alkyl
R$^1$ = H or C$_6$ to C$_{12}$ Alkyl
n = 1 to 20

(4) Ester Ethoxylates

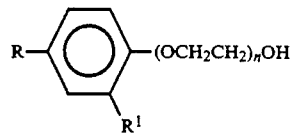

R = C$_6$ to C$_{20}$
n = 1 to 20

(5) Alkyl Aryl polyethoxylated phosphate esters

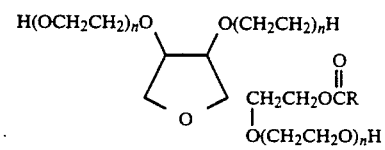

R = C$_6$–C$_{12}$
n = 4 to 6

(6) Block Copolymers

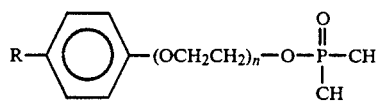

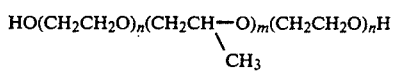

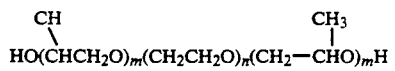

n = 1 to 20 moles of ethylene oxide
m = 1 to 20 moles of propylene glycol (7) Alkyl Benzene Sulfonates

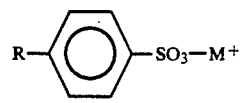

R = linear C$_1$–C$_6$ alkyl group
M+ = counter ion—(Ca$^{+2}$, Mg$^{+2}$) (Na$^{+1}$)

The formulations of this invention provide an improved method of diluting dimethoate concentrates for application to plants in order to control damage caused by several species of insects and mites. A detailed listing of those pests controlled by dimethoate can be found in U.S. Pat. No. 3,987,169. For applications by equipment on the ground, typically about 3 to about 51.2 ounces are used in 5–400 gallons of spray solution per acre. If application is being made by aerial equipment, about 3 to about 51.2 ounces should be applied in 5–15 gallons of water. In both cases, the formulation concentration should not exceed 7.0% by volume.

The following Examples are illustrative of the invention but are not intended in any way to place any limitations on the scope of the invention.

Example 1

A water soluble dimethoate concentrate containing 5 lb. per gallon dimethoate was prepared at room temperature by mixing the following ingredients with mild stirring in a 2 liter glass beaker:

| Component | % | Grams Per Liter |
|---|---|---|
| Dimethoate | 60.0 | 630.0 |
| Ethyl Alcohol (anhydrous) | 33.0 | 346.5 |
| Ethyl Acetate (anhydrous) | 7.0 | 73.5 |
| | 100.0 | 1,050.0 |

For ease of mixing, the following addition order is preferred: (1) Ethyl Alcohol—(2) Ethyl Acetate—(3) Dimethoate. After 25 minutes of mild agitation, a clear solution resulted exhibiting the following chemical and physical properties:

| Parameter | Results |
|---|---|
| % Dimethoate | 57.0 |
| Grams of Dimethoate/liter | 598.5 |
| Lbs. of Dimethoate/gallon | 5.0 |
| Grams per ml | 1.050 |
| Water solubility | 6.5 gms/100 cc |
| Water miscibility | 100% |
| Degradation Test @ 30 days @ 45° C. | (less than 2.0% dimethoate decomposition) |
| Freeze Point | 38° F. |

Example 2

A water soluble dimethoate concentrate containing 4 lb. per gallon dimethoate was prepared at room temperature by mixing the following ingredients with mild stirring in a 2 liter glass beaker:

| Component | % | Grams Per Liter |
|---|---|---|
| Dimethoate (95) | 44.70 | 471.6 |
| Ethyl Alcohol (anhydrous) | 41.40 | 436.4 |
| Ethyl Acetate (anhydrous) | 13.90 | 147.1 |
| | 100.00 | 1,055.1 |

After 25 minutes of mild agitation, a clear solution resulting exhibiting the following chemical and physical properties:

| Parameter | Results |
|---|---|
| % Dimethoate | 42.5 |
| Grams of Dimethoate/liter | 448 |
| Lbs. of Dimethoate/gallon | 4.0 |
| Grams per ml | 1.055 |
| Water solubility | 7 gms/100 cc |
| Water miscibility | 100% |
| Degradation Test @ 30 days @ 45° C. | (less than 2.0% dimethoate decomposition) |
| Freeze Point | 34° F. |

Example 3

A water soluble dimethoate concentrate containing 2.67 lb. per gallon dimethoate was prepared at room temperature by mixing the following ingredients with mild stirring in a 2 liter glass beaker:

| Component | % | Grams Per Liter |
|---|---|---|
| Dimethoate (95) | 32.1 | 336.7 |
| Ethyl Alcohol (anhydrous) | 10.0 | 104.9 |
| Ethyl Acetate (anhydrous) | 57.9 | 607.4 |
| | 100.00 | 1,049.0 |

After 25 minutes of mild agitation, a clear solution resulting exhibiting the following chemical and physical properties:

| Parameter | Results |
|---|---|
| % Dimethoate | 30.5 |
| Grams of Dimethoate/liter | 320 |
| Lbs. of Dimethoate/gallon | 2.67 |
| Grams per ml | 1.049 |
| Water solubility | 7.6 gms/100 cc |
| Water miscibility | 100% |
| Degradation Test @ 30 days @ 45° C. | (less than 1% decay) |
| Freeze Point | less than 32° F. |

Comparative Example A

A composition (Composition A) containing the ingredients shown below was prepared following the process used in Examples 1, 2 and 3. The ethyl alcohol utilized in Examples 1, 2 and 3 was substituted with the solvent system utilized in conventional dimethoate formulations.

| Component | % | Grams Per Liter |
|---|---|---|
| Dimethoate (95) | 60.0 | 613.2 |
| Xylene range hydrocarbons | 33.0 | 337.3 |
| Ethyl Acetate | 7.0 | 71.5 |
| | 100.00 | 1,022.0 |

After 25 minutes of mild agitation, the resulting mixture was turbid and found not to be a complete solution. This situation remained even after additional vigorous agitation of the mixture's components. This indicates that a solution of dimethoate equivalent to that of Example 1 was not possible without the ethanol.

The incomplete solution produced by Comparative Example A was allowed to stand undisturbed. A sample of the clear liquid remaining after the undissolved dimethoate had settled out was collected and evaluated for the parameters described in Examples 1, 2 and 3.

| Parameter | Results |
|---|---|
| % Dimethoate | 39.7 |
| Grams of Dimethoate/liter | 397.0 |
| Lbs. of Dimethoate/gallon | 3.3 |
| Grams per ml | 1.0 |

| Parameter | Results |
|---|---|
| Water solubility | less than 2.0 gms/100 ml |
| Water miscibility | zero |
| Degradation Test @ 30 days @ 45° C. | less than 1% |
| Freeze Point | 40° F. |

Comparative Example B

A composition (Composition B) containing the ingredients shown below was prepared following the process in Example 1. The ethyl acetate utilized in Example 1, however, was replaced with additional ethanol.

| Component | % | Grams Per Liter |
|---|---|---|
| Dimethoate 95 | 60.00 | 606.0 |
| Ethyl Alcohol (anhydrous) | 40.00 | 404.0 |
| | 100.00 | 1,010.0 |

After 25 minutes of mild agitation, the resulting mixture was turbid and not in complete solution. Additional agitation was applied for 25 minutes longer and a clear solution was obtained. It was noted, however, that 3-5% of the dimethoate remained undissolved.

A sample of the solution was removed from the mixture and evaluated for the following parameters:

| Parameter | Results |
|---|---|
| % Dimethoate | 52.1 |
| Grams of Dimethoate/liter | 526 |
| Lbs. of Dimethoate/gallon | 4.3 |
| Grams per ml | 1.010 |
| Water solubility | 8 grams/liter |
| Water miscibility | 100% |
| Degradation Test @ 30 days @ 45° C. | 2.5% |
| Freeze Point | 41° F. |

A review of the values exhibited by Comparative Examples A and B reveals significant differences between those of Example 1. These differences point out the advantages of utilizing the formulation outlined in Example 1. These advantages are outlined by the following table:

| Parameter | Example 1 | Comparative Example A | Comparative Example B |
|---|---|---|---|
| % Maximum dimethoate con. | 57.0 | 39.7 | 52.1 |
| Maximum lbs. of dimethoate per gallon | 5.0 | 3.3 | 4.3 |
| Water miscibility | 100% | zero | 100% |
| Maximum water solubility in grams/ 100 ml | 6.5 | 2.0 | 8.0 |
| Freeze Point in °F. | 36° F. | 40° F. | 41° F. |
| % Dimethoate degradation @ 45° C. for thirty days | 2.0 | 1.0 | 2.5 |

Comparison of the above values shows that Example 1 offers higher levels of dimethoate concentration, 100% water miscibility, lower temperature stability, and enhanced water solubility when compared to the values found for Comparative Example A. Even though Comparative Example B provides both enhanced water solubility and miscibility, the omission of the acetate ester from the formulation limits the maximum amount of dimethoate concentration and raises the composition's freeze point.

The solvent system of Example 1 significantly enhanced the solubility of dimethoate in water. The maximum solubility of dimethoate in water reported in the literature is 25 grams per liter at 21° C. (*Agrochemicals Handbook*, 2nd Ed. Royal Society of Chemists 1987). This solubility limit is raised by employing the solvent system described in Example 1. This characteristic is illustrated by the following solubility results:

Test solutions of known dimethoate concentration were prepared in distilled water buffered to a pH of 2.1. These solutions were maintained at ambient temperature (73° F.±1° F.) and analyzed by Gas Liquid Chromatography (GLC) for actual dimethoate content. The % solution is the amount of "pure" dimethoate used to prepare the test solution. This "pure" dimethoate was reported by the manufacturer to contain 98.0% dimethoate. The theoretical % is obtained by multiplying the % solution by the amount of dimethoate (0.98). The actual % dimethoate is the value analyzed by GLC. The accuracy of the method utilized was determined to be ±2% so the actual amounts can exceed the theoretical amounts. These values were compared to the theoretical ones and categorized in the table below:

| | Dimethoate Solubility | | |
|---|---|---|---|
| % Solution by Weight | Theoretical % Dimethoate by Weight | Actual Dimethoate by Weight | Dimethoate Solubility in grams per liter |
| 1.0 | .98 | .95 | 9.5 |
| 2.0 | 1.96 | 2.10 | 21.0 |
| 3.0 | 2.94 | 2.20 | 22.0 |
| 4.0 | 3.92 | 2.50 | 25.0 |
| 5.0 | 4.90 | 2.30 | 23.0 |
| 6.0 | 5.90 | 2.50 | 25.0 |
| 7.0 | 6.86 | 2.10 | 21.0 |
| 8.0 | 7.84 | 2.50 | 25.0 |

The following table shows the solubility of the dimethoate formulation prepared in Example 1 containing 57.0% by weight dimethoate

| Dimethoate Solubility of Formulation of Example 1 | | | |
|---|---|---|---|
| % Solution by Weight | Theoretical % Dimethoate by Weight | Actual Dimethoate by Weight | Solubility in grams per liter |
| 3.0 | 1.71 | 1.78 | 17.8 |
| 4.0 | 2.30 | 2.21 | 22.1 |
| 5.0 | 2.85 | 2.90 | 29.0 |
| 6.0 | 3.42 | 3.41 | 34.1 |
| 7.0 | 3.99 | 3.75 | 37.5 |
| 8.0 | 4.60 | 3.70 | 37.0 |
| 9.0 | 5.10 | 3.60 | 36.0 |

The % solution is the amount of dimethoate formulation used to prepare the test solution. The theoretical % is obtained by multiplying the % solution by the amount of dimethoate in the formulation (0.57). The actual % dimethoate is the value analyzed by GLC. The accuracy of the method utilized was determined to be ±1-5%.

The dimethoate solubility achieved with the formulations of Example 1 ranged from 34.1 to 37.5 grams per liter at its maximum limit. This is 27-28% higher than the 25 grams per liter reported for dimethoate in water in *Agrochemicals Handbook*.

What is claimed is:

1. An insecticide formulation consisting essentially of an effective amount of O,O-dimethyl S-(N-methylcarbamyl) phosphorodithioate in a solvent system comprising an effective amount of the mixture of an aliphatic $C_1$–$C_4$ alcohol and an acetate ester of an aliphatic $C_1$–$C_4$ alcohol.

2. A formulation according to claim 1 wherein the alcohol is methanol, ethanol, propanol, isopropanol or butanol.

3. A formulation according to claim 1 wherein the ester is methyl acetate, ethyl acetate, propyl acetate or butyl acetate.

4. A formulation according to claim 1 consisting essentially of about 1.0% to about 70.0% by weight of O,O-dimethyl S-(N-methylcarbamyl) phosphorodithioate based on the weight of the formulation.

5. A formulation according to claim 1 comprising from about 99% to about 30% by weight of the ester/alcohol solvent system based on the weight of the formulation.

6. A formulation according to claim 1 comprising from about 40% to about 60% by weight of the ester/alcohol solvent system based on the weight of the formulation.

7. A formulation according to claim 1 wherein the ester and alcohol are present in the weight ratio from 5:95 to 95:5.

8. A formulation according to claim 1 wherein the ester and alcohol are present in the weight ratio from 17.5:82.5.

9. A formulation according to claim 1 wherein the alcohol is ethanol and the ester is ethyl acetate.

10. An insecticide formulation consisting essentially of about 45 to about 60 % by weight based on the weight of the formulation of O,O-dimethyl S-(N-methylcarbamyl) phosphorodithioate in a solvent mixture of ethyl acetate and ethanol present in a weight ratio of 20:80.

* * * * *